United States Patent
Nishimura et al.

(10) Patent No.: US 12,350,070 B2
(45) Date of Patent: Jul. 8, 2025

(54) BIOLOGICAL INFORMATION MEASUREMENT DEVICE

(71) Applicant: Fukuda Denshi Co., Ltd., Tokyo (JP)

(72) Inventors: Naoki Nishimura, Saitama (JP); Yuki Miyauchi, Kochi (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 1320 days.

(21) Appl. No.: 15/759,236

(22) PCT Filed: Sep. 8, 2016

(86) PCT No.: PCT/JP2016/076518
§ 371 (c)(1),
(2) Date: Mar. 12, 2018

(87) PCT Pub. No.: WO2017/043603
PCT Pub. Date: Mar. 16, 2017

(65) Prior Publication Data
US 2020/0229706 A1    Jul. 23, 2020

(30) Foreign Application Priority Data
Sep. 11, 2015    (JP) .................................. 2015-179595

(51) Int. Cl.
*A61B 5/05*     (2021.01)
*A61B 5/00*     (2006.01)
(Continued)

(52) U.S. Cl.
CPC ............ *A61B 5/6832* (2013.01); *A61B 5/024* (2013.01); *A61B 5/263* (2021.01); *A61B 5/274* (2021.01);
(Continued)

(58) Field of Classification Search
CPC ......... A61B 5/282; A61B 5/0006; A61B 5/25; A61B 5/349; A61B 5/318; A61B 5/259;
(Continued)

(56) References Cited

U.S. PATENT DOCUMENTS

| | | | |
|---|---|---|---|
| 5,483,967 | A | 1/1996 | Ohtake |
| 2003/0149349 | A1 | 8/2003 | Jensen |

(Continued)

FOREIGN PATENT DOCUMENTS

| | | |
|---|---|---|
| CN | 103025233 A | 4/2013 |
| JP | 64-042008 U | 3/1989 |

(Continued)

OTHER PUBLICATIONS

International Search Report from International Application No. PCT/JP2016/076518 mailed Dec. 6, 2016.
(Continued)

*Primary Examiner* — Joseph A Stoklosa
*Assistant Examiner* — Brian M Antiskay
(74) *Attorney, Agent, or Firm* — Shih IP Law Group, PLLC

(57) ABSTRACT

A terminal (300) is attached to a sensor sheet (100) using a tongue piece (131) that extends from the sensor sheet (100). This makes it possible to reduce a sense of discomfort in a subject caused by the presence of the terminal (300), and to realize a biological-information measurement device with which it is possible to mitigate a sense of discomfort in a subject caused by the device, to a greater extent than in a case in which, e.g., the entire reverse surface of the terminal (300) is secured to the sensor sheet (100).

12 Claims, 5 Drawing Sheets

(51) Int. Cl.
*A61B 5/024* (2006.01)
*A61B 5/263* (2021.01)
*A61B 5/274* (2021.01)
*A61B 5/28* (2021.01)

(52) U.S. Cl.
CPC ........ *A61B 5/28* (2021.01); *A61B 2560/0406* (2013.01); *A61B 2562/0295* (2013.01)

(58) Field of Classification Search
CPC .............. A61B 5/02438; A61B 5/6831; A61B 2562/0215; A61B 5/332; A61B 5/6833; A61B 2560/0412; A61B 5/6804; A61B 5/0002; A61B 5/24; A61N 1/0492
USPC .......................... 600/372, 382–393, 508–509
See application file for complete search history.

(56) References Cited

U.S. PATENT DOCUMENTS

| | | | | |
|---|---|---|---|---|
| 2008/0139953 | A1* | 6/2008 | Baker | A61B 5/024 600/509 |
| 2008/0288026 | A1* | 11/2008 | Cross | H01R 13/24 607/60 |
| 2010/0228113 | A1* | 9/2010 | Solosko | A61N 1/048 600/382 |
| 2011/0144470 | A1* | 6/2011 | Mazar | A61B 5/257 600/391 |
| 2011/0237922 | A1* | 9/2011 | Parker, III | A61B 5/1112 600/382 |
| 2013/0060115 | A1* | 3/2013 | Gehman | A61B 5/274 600/372 |
| 2013/0116534 | A1 | 5/2013 | Woo | |
| 2013/0131484 | A1* | 5/2013 | Pernu | A61B 5/28 600/388 |
| 2015/0082623 | A1* | 3/2015 | Felix | A61B 5/273 29/825 |
| 2015/0094558 | A1* | 4/2015 | Russell | A61B 5/0022 600/391 |
| 2015/0351689 | A1* | 12/2015 | Adams | A61B 5/6833 600/300 |
| 2016/0302684 | A1* | 10/2016 | en-Haim | A61B 5/282 |
| 2018/0049698 | A1* | 2/2018 | Berg | A41D 1/005 |
| 2021/0401373 | A1* | 12/2021 | Yang | A61B 5/02055 |

FOREIGN PATENT DOCUMENTS

| | | |
|---|---|---|
| JP | 02-055918 U | 4/1990 |
| JP | 06-245915 A | 9/1994 |
| JP | 2001-269322 A | 10/2001 |
| JP | 2015-112144 A | 6/2015 |
| WO | 2007063436 A1 | 6/2007 |
| WO | 2014057083 A2 | 4/2014 |
| WO | 2014116816 A1 | 7/2014 |

OTHER PUBLICATIONS

European Search Report for EP 16844464.4 mailed May 9, 2019, 7 pages.

* cited by examiner

BIOLOGICAL INFORMATION MEASUREMENT DEVICE

TECHNICAL FIELD

The present invention relates to a biological information measurement apparatus that measures biological information using a sensor sheet applied to the skin of a subject.

BACKGROUND ART

Conventionally, there are apparatuses that measures biological information of a subject by a sensor sheet with a sensor incorporated therein applied to the body surface of the subject. For example, in the case of electrocardiographic measurement apparatuses, an electrocardiogram of a subject is obtained via electrodes incorporated in a sensor sheet (see Patent Literatures 1 and 2).

In the sensor sheet (biological electric signal recording device) disclosed in Patent Literature 1, electrodes are provided in a sheet-like base material that is flexible enough to follow movements of a living body, and the electrodes are surrounded in a watertight manner by the sheet-like base material, such that measurement of electrocardiograms can be made even during bathing in addition to walking, eating and sleeping.

CITATION LIST

Patent Literature

PTL 1
  Japanese Patent Application Laid-Open No. HEI 6-245915
PTL 2
  Japanese Patent Application Laid-Open No. 2001-269322

SUMMARY OF INVENTION

Technical Problem

A sensor sheet is provided with a terminal including, e.g., a memory attached thereto. For example, the terminal includes contacts for connection to a sensor sheet, a memory that stores biological information input from the sensor sheet through the contacts, and an external contact for outputting the information stored in the memory to an external device.

When a biological information measurement apparatus including a sensor sheet and a terminal such as the above is used to obtain a Holter electrocardiogram for example, it is necessary that the biological information measurement apparatus including a sensor sheet and a terminal be continuously applied to the chest region over a long period of time. For example, in a follow-up after an ablation treatment, continuous data of no less than two weeks is supposed to be obtained, and in this case, a sensor sheet is supposed to be continuously applied to the body surface of a subject over no less than two weeks.

Therefore, it is necessary to minimize a feeling of discomfort the subject has when the subject wears the biological information measurement apparatus.

The present invention has been made in view of the above points and provides a biological information measurement apparatus that can reduce a feeling of discomfort a subject has when the subject wears the biological information measurement apparatus.

Solution to Problem

An aspect of the present invention provides a biological information measurement apparatus including: a sensor sheet to be applied to a skin of a subject; a terminal to be attached to the sensor sheet, in which the terminal is attached to the sensor sheet so as to be at least partially floated from the sensor sheet by a tongue piece.

Advantageous Effects of Invention

According to the present invention, a terminal is attached to a sensor sheet so as to be at least partially floated from the sensor sheet by a tongue piece, and thus the area of the part of the terminal, the part being in abutment with the sensor sheet, can be reduced, and as a result, a biological information measurement apparatus that can reduce a feeling of discomfort a subject has when the subject wears the biological information measurement apparatus can be provided.

BRIEF DESCRIPTION OF DRAWINGS

FIG. 3A is a perspective view, FIG. 3B is a side view, and FIG. 3C is a bottom view;

FIG. 4A is a cross-sectional view before attachment, and FIG. 4B is a cross-sectional view after attachment; FIG. 5A is a cross-sectional view before attachment, and FIG. 5B is a cross-sectional view after attachment.

DESCRIPTION OF EMBODIMENTS

Embodiments of the present invention will be described in detail below with reference to the accompanying drawings.

Overall Configuration

Figure 1:
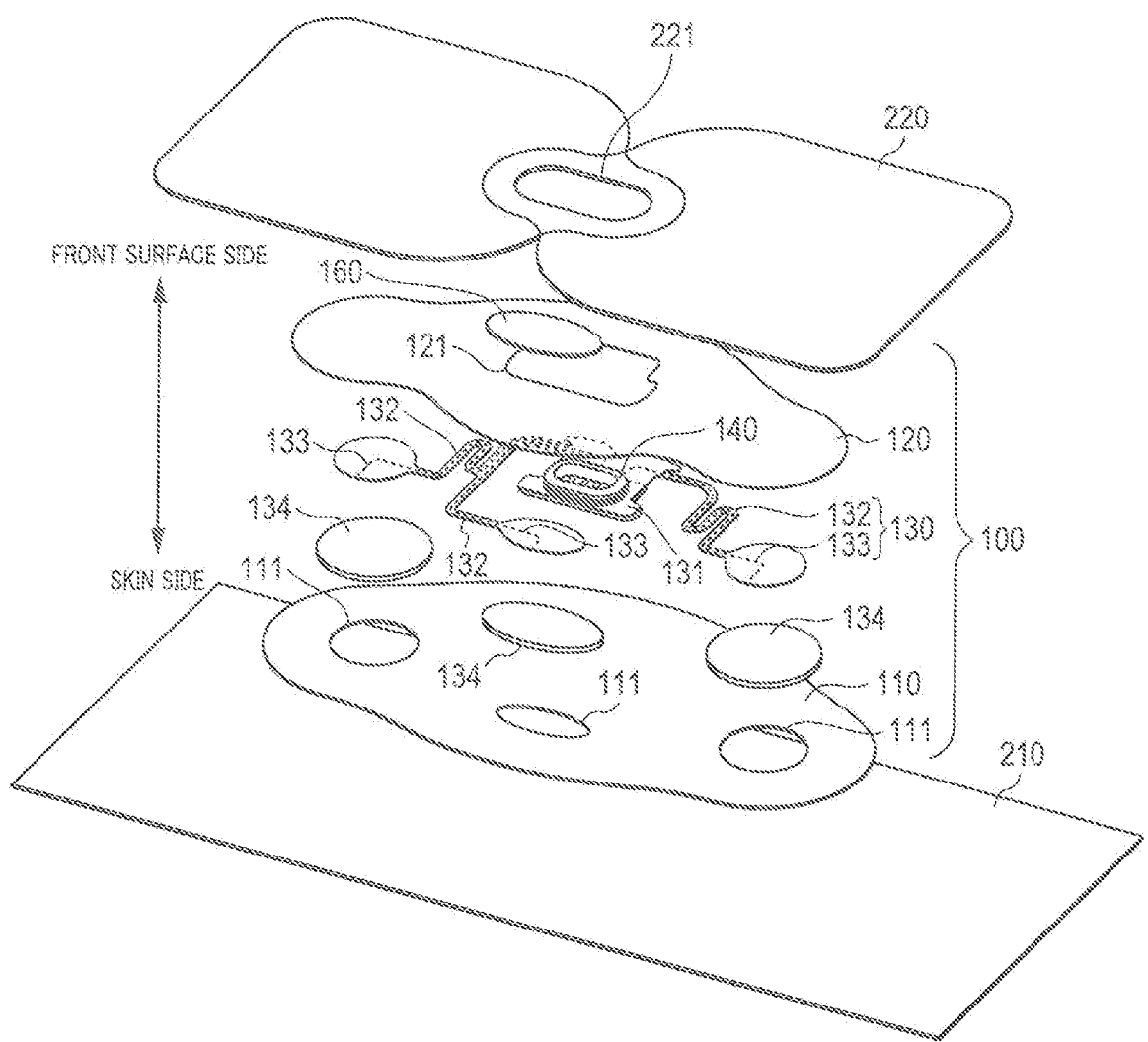
FIG. 1 is an exploded perspective view illustrating an overall configuration of a sensor sheet.
Figure 2:
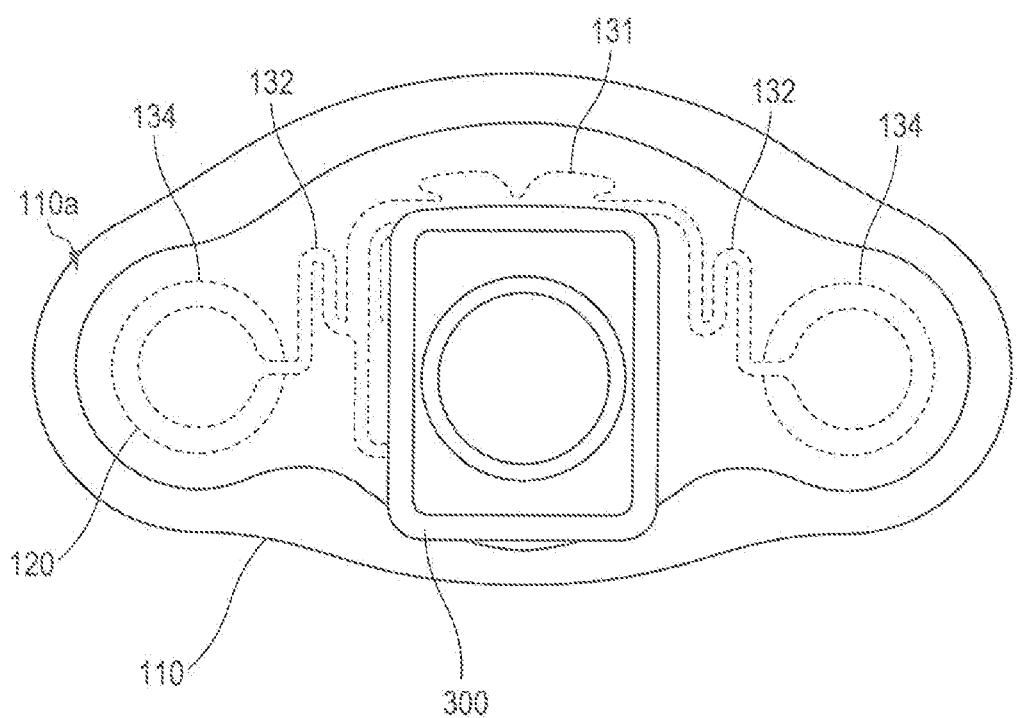
FIG. 2 is a top view of the sensor sheet with a terminal is attached thereto.

FIG. 1 is an exploded perspective view illustrating an overall configuration of a sensor sheet according to Embodiment of the present invention. FIG. 2 is a top view of the sensor sheet with a terminal attached thereto. The sensor sheet is attached to the chest region of a subject and used to obtain an electrocardiogram.

The present embodiment will be described in terms of a case where a terminal to be attached to a sensor sheet is a recording terminal including a memory and a coin cell housed inside a case thereof; however, the terminal to be attached to the sensor sheet is not limited to this type of terminal. For example, the terminal may be a terminal that includes a wireless transmission section inside a case and wirelessly transmits biological information measured by the sensor sheet. Also, the terminal may be, for example, a telemeter.

As illustrated in FIG. 1, before use, sensor sheet 100 is held between liner 210 and top separator 220. Then, in use, liner 210 and top separator 220 are removed and sensor sheet 100 is applied to the chest region, and as illustrated in FIG. 2, terminal 300 is attached to the front surface side.

Sensor sheet 100 includes lower sheet (first sheet) 110 and upper sheet (second sheet) 120. Electric circuit section 130, which serves as a measuring element, is disposed between lower sheet 110 and upper sheet 120. An adhesion layer is provided on a surface on the skin side of each of lower sheet 110 and upper sheet 120, and consequently, lower sheet 110 is to be applied to the skin of a subject and upper sheet 120 is stuck to the front surface side of lower sheet 110. Electric circuit section 130 is held between lower sheet 110 and upper sheet 120 as a result of upper sheet 120 being stuck to the front surface side of lower sheet 110.

Upper sheet 120 is smaller in area than lower sheet 110. The area of upper sheet 120 is large enough to cover electric circuit section 130. More specifically, as can be seen from FIG. 2, which illustrates upper sheet 120 stuck to lower sheet 110, peripheral edge portion 110a, which is formed of lower sheet 110 alone, is formed over an entire circumference of sensor sheet 100 while electric circuit section 130 is fully covered by upper sheet 120.

Electric circuit section 130 includes tongue piece 131, a plurality of wires 132 extending from tongue piece 131, and a plurality of electrodes 133 formed at terminal ends of respective wires 132.

Holes 111 are formed at positions in lower sheet 110 that correspond to respective electrodes 133, and gels 134 are disposed at positions corresponding to respective holes 111. Consequently, electrodes 133 are electrically connected to the skin via gels 134, and electric conductivity between the skin and electrodes 133 is enhanced by gels 134.

Connector 140 to be connected to terminal 300 is provided on the front surface side of tongue piece 131. Hole 121 is formed at a position in upper sheet 120, the position corresponding to tongue piece 131. Consequently, in a state in which upper sheet 120 is stuck to lower sheet 110, tongue piece 131 is exposed on the front surface side of upper sheet 120 via hole 121.

Furthermore, hole 221 is formed at a position in top separator 220, the position corresponding to connector 140. Consequently, connector 140 is exposed on the front surface side of top separator 220 via hole 221.

Here, lower sheet 110 includes a base material formed of polyurethane and the adhesion layer formed on the surface on the skin side of the base material. Likewise, upper sheet 120 includes a base material formed of polyurethane and the adhesion layer formed on the surface on the skin side of the base material. As described above, sheets 110, 120 are each formed of polyurethane having a high moisture vapor permeability, enabling suppression of a skin rash caused by sweating and thus enabling suppression of itching caused by a rash.

For further information, polyurethane has the characteristic of transmitting water vapor and not transmitting collected water (that is, transmitting small particles such as water vapor, but not transmitting a large mass of water such as collected water or a water droplet), and thus, when the subject takes a bath, there is almost no permeation of water from the front surface side to the skin side of upper sheet 120. Therefore, entry of water from the front surface side of upper sheet 120 to wires 132 and electrodes 133 can be suppressed, enabling prevention of a short in the electric circuit even when the subject takes a bath with sensor sheet 100 applied.

Although in the present embodiment, lower sheet 110 and upper sheet 120 are both formed of polyurethane, itching is likely to occur particularly at a peripheral edge portion of a sheet, and thus, it is possible that: only lower sheet 110 including peripheral edge portion 110a is formed of polyurethane; and upper sheet 120 is formed of a material other than polyurethane. Furthermore, for materials of lower sheet 110 and upper sheet 120, any of various materials other than polyurethane can be used as long as such materials are ones that can prevent entry of water that causes a short in wires 132 and electrodes 133 while transmitting moisture resulting from sweating. For example, foamed polyethylene or a non-woven material may be used. Also, lower sheet 110 and upper sheet 120 are not necessarily formed of polyurethane alone, and may be formed of a material containing polyurethane as a main component.

However, the inventors found out that polyurethane is most excellent for materials of lower sheet 110 and upper sheet 120. Here, for lower sheet 110 and upper sheet 120, for example, almost no permeation of water from the front surface side to the skin side of upper sheet 120 when the subject takes a bath (that is, waterproof property), the capability of being used for a long period of time without being torn (that is, durability), a flexibly enabling following movements of the skin (that is, stretchability), and the capability of being thinned are required. Polyurethane is desirable in all of waterproof property, durability, stretchability and the capable of being thinned On the other hand, foamed polyethylene is poor in durability and the capability of being thinned. Non-woven fabric is poor in waterproof property.

Lower sheet 110 in the present embodiment has a thickness of 15 [μm]. This thickness is much smaller than a thickness of around 50 [μm], which is a thickness of a conventional sheet of this type. On the other hand, upper sheet 120 has a thickness that is larger than that of lower sheet 110. In the case of the present embodiment, upper sheet 120 has a thickness of 50 [μm]. In other words, in the case of the present embodiment, while peripheral edge portion 110a formed of lower sheet 110 alone has a thickness of 15 [μm] and thus, is very thin, a center area in which electric circuit section 130 is held has a thickness of 65 [μm] including the thicknesses of lower sheet 110 and upper sheet 120. Consequently, even if peripheral edge portion 110a is very thin, the center area in which electric circuit section 130 is held is thick, enabling a measurement accuracy decrease to be prevented without a decrease in reliability of electric circuit section 130.

In particular, it is desirable that upper sheet 120 be made to be thicker than lower sheet 110. In other words, it is only necessary to form upper sheet 120 so as to be higher in strength than lower sheet 110. For example, upper sheet 120 may be formed of a material having a strength that is higher than that of lower sheet 110.

The reason why a conventional sheet has a large thickness including a peripheral edge portion thereof is that a priority is placed on suppression of damage of the sheet and highly reliable holding of electric circuit section 130, which serves as a measuring element, and no sufficient consideration is given to itching caused when the sheet is continuously applied for a long period of time.

In the present embodiment, paying attention to the point that itching can substantially be reduced if peripheral edge portion 110a follows the skin, lower sheet 110 was studied in terms of material and thickness. As a result, it has been found that if lower sheet 110 is formed of polyurethane in consideration of moisture vapor permeability, itching is less likely to occur even if lower sheet 110 is continuously applied for around two weeks as long as lower sheet 110 has a thickness of no more than 20 [μm]. In other words, in the present embodiment, forming lower sheet 110 from polyurethane and making lower sheet 110 have a thickness of no more than 20 [μm] are proposed.

Also, as described above, lower sheet 110 is made to have a very small thickness of no more than 20 [μm] and is thus superior in following the skin, which provides the advantage of enabling provision of a sheet that is less likely to come off in addition to suppression of itching. In other words, a sheet almost always starts coming off at a peripheral edge portion and thus, can be prevented from coming off by the configuration provided by the present embodiment.

Wires 132 and electrodes 133 are configured by forming a metal layer on a base material formed of, e.g., PET (polyethylene terephthalate) or PEN (polyethylene naphthalate). The base material has a thickness of, for example, around 50 to 100 [μm]. It is also possible that wires 132 and electrodes 133 are formed directly on upper sheet 120 or lower sheet 110; however, in the case of the present embodiment, wires 132 and electrodes 133 are formed on, e.g., the base material formed of, e.g., PET (polyethylene terephthalate) or PEN (polyethylene naphthalate), enabling prevention of occurrence of, e.g., disconnection.

Here, the base material formed of, e.g., PET (polyethylene terephthalate) or PEN (polyethylene naphthalate) is less flexible than polyurethane, which is the material of lower sheet 110 and upper sheet 120. Therefore, in the case of the present embodiment, wires 132 have a pattern including a meandering pattern. Consequently, wires 132 follows movements of the body surface (skin) well. As a result, the capability of following the skin can be enhanced also in the area of electric circuit section 130, as well as peripheral edge portion 110a, enabling further suppression of occurrence of itching. However, wires 132 do not necessarily need to be made to meander, and wires 132 may be formed in a shallow curve or a linear fashion.

Tongue piece 131 is thicker than the base material of wires 132 and electrodes 133. Terminal 300 is detachably attached to connector 140 provided on tongue piece 131. A structure of the attachment of connector 140 to terminal 300 will be described later.

Next, a procedure for applying sensor sheet 100 to the chest region of a subject will be described.

When sensor sheet 100 is applied to a predetermined position in the chest region, first, liner 210 is removed and sensor sheet 100 is pressed against the predetermined position in the chest region together with top separator 220 to apply lower sheet 110 to the predetermined position in the chest region.

Top separator 220 is rubbed from above in this state, whereby lower sheet 110 is firmly applied to the skin of the subject. For further information, an adhesion layer having a small adhesive force enough to hold sensor sheet 100 is formed on a lower surface of top separator 220.

The provision of top separator 220 enables prevention of twisting of peripheral edge portion 110a of very thin lower sheet 110. Hole 221 for avoiding connector 140 is formed at a center of top separator 220. A user holds areas in the periphery of hole 221 between his/her fingers and separate and peel back top separator 220 so as to be separated and removed outward like opening a double door, whereby top separator 220 is removed from sensor sheet 100. As described above, as a result of top separator 220 being removed from sensor sheet 100 from the center to the edge side of sensor sheet 100, rather than from the edge side, lower sheet 110 is strained by top separator 220, enabling reduction in possibility of the edge of lower sheet 110 peeling off and wrinkling.

After sensor sheet 100 is applied to the chest region to the subject in this way, the user attaches terminal 300 to connector 140 of sensor sheet 100.

Attachment Structure in Terminal 300 for Attaching Terminal 300 to Sensor Sheet 100

Figure 3A:
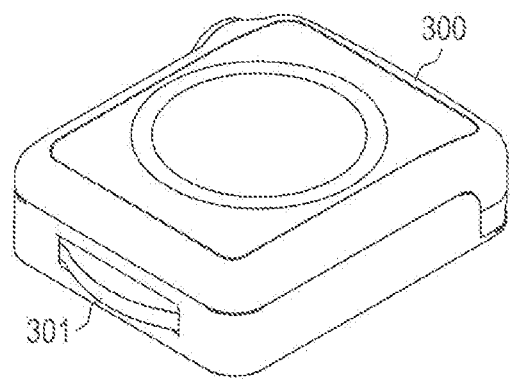
FIGS. 3A, 3B and 3C are diagrams illustrating a configuration of the terminal.
Figure 3B:
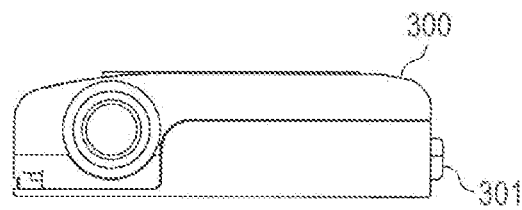
Figure 3C:
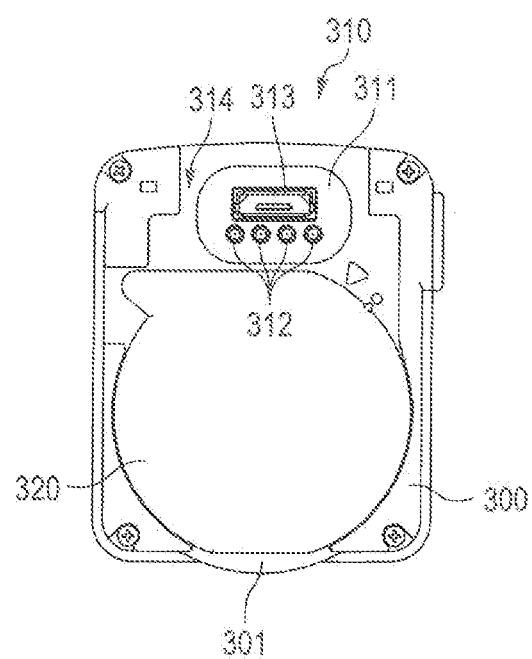

FIGS. 3A, 3B and 3C are diagrams illustrating a configuration of terminal 300; FIG. 3A is a perspective view, FIG. 3B is a side view and FIG. 3C is a bottom view.

Terminal 300 includes, e.g., a coin cell and a memory incorporated therein. Upon power supply button 301 being pressed, terminal 300 starts an electrocardiographic measurement and recording operation, and records an electrocardiogram based on an electrocardiographic signal from the sensor sheet. This measurement and recording operation is a known technique and thus, description thereof will be omitted.

As illustrated in FIG. 3C, attachment section 310 to be detachably attached to connector 140 provided in sensor sheet 100 is provided in a back surface of terminal 300.

Figure 4A:
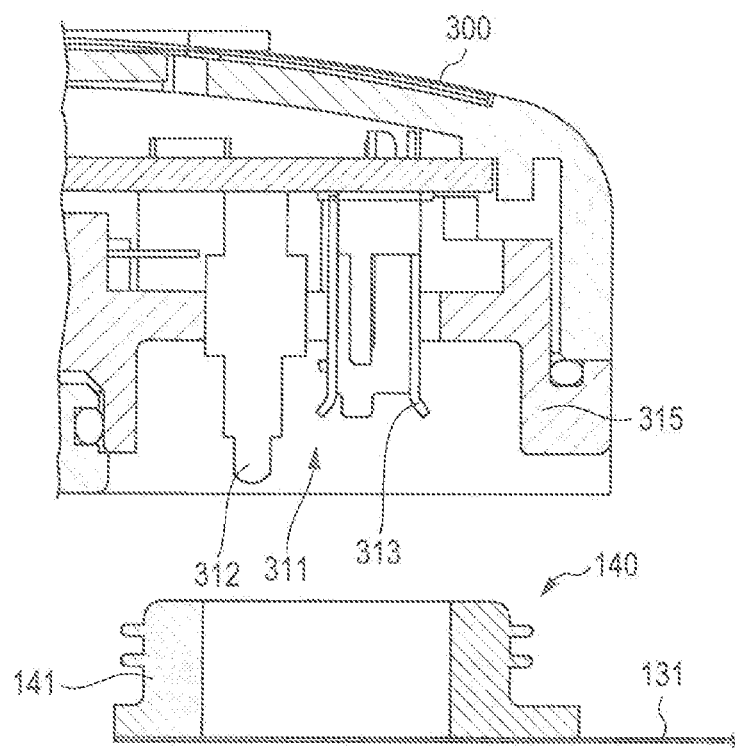
FIGS. 4A and 4B are cross-sectional views for description of an attachment structure in the terminal for attaching the terminal to the sensor sheet.
Figure 4B:
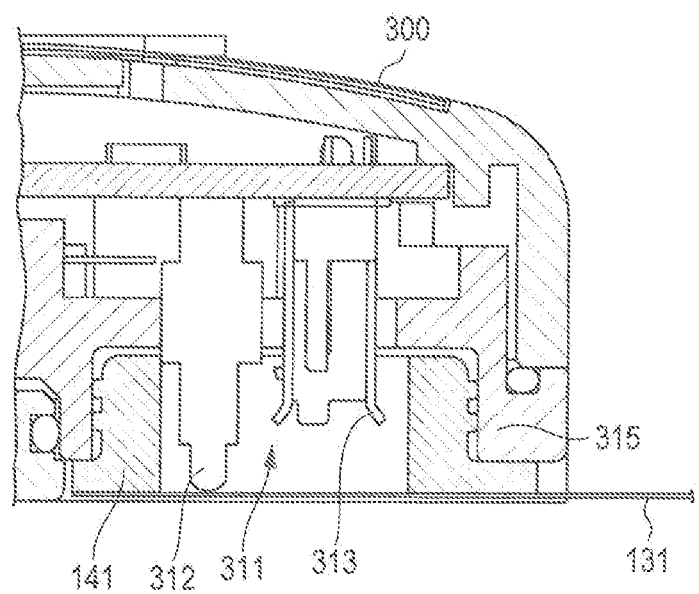

FIGS. 4A and AB are cross-sectional views for description of an attachment structure in terminal 300 for attaching terminal 300 to sensor sheet 100. FIG. 4A is a cross-sectional view before attachment, and FIG. 4B is a cross-sectional view after attachment.

Figure 5A:
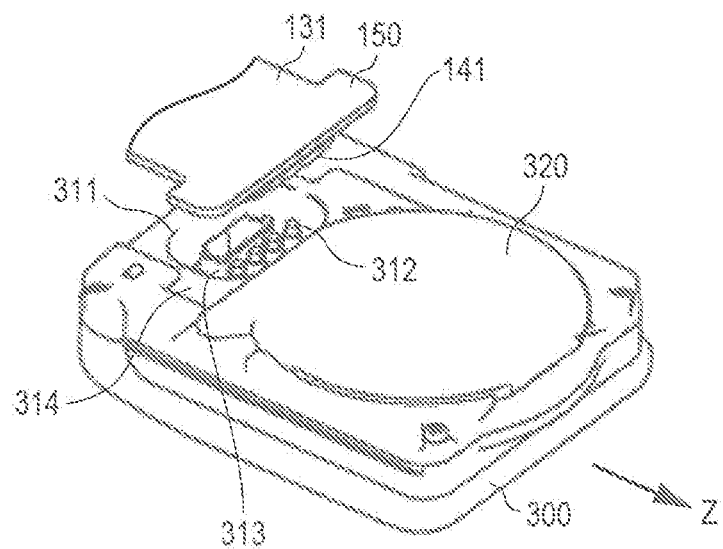
FIGS. 5A and 5B are perspective views for description of an attachment structure in the terminal for attaching the terminal to the sensor sheet.
Figure 5B:
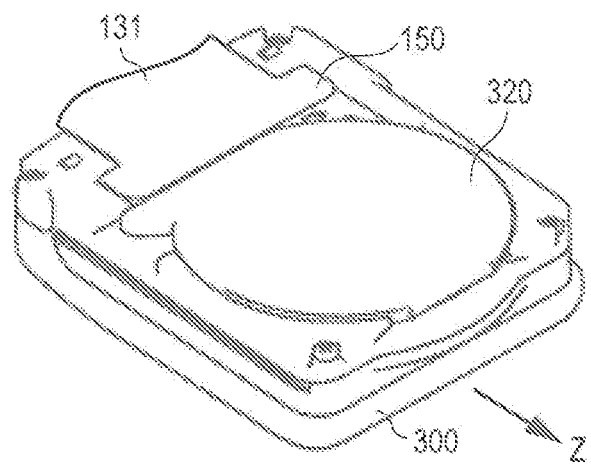

FIGS. 5A and 5B are perspective views for description of an attachment structure in terminal 300 for attaching terminal 300 to sensor sheet 100, FIG. 5A is a perspective view before attachment, and FIG. 5B is a perspective view after attachment.

Here, connector 140 provided on the sensor sheet 100 side includes packing 141 having an oval shape in plan view. Terminal ends of wires 132, other ends of which are connected to respective electrodes 133, are disposed on an area in tongue piece 131, the area being surrounded by packing 141.

Also, insertion opening 311 having a size that allows packing 141 to be just fitted therein is formed in the back surface of terminal 300. Inside insertion opening 311, spring probes 312 and USB port 313 are disposed. More specifically, as illustrated in FIGS. 4A and 4B, shield frame 315 is formed in the back surface of terminal 300, and shield frame 315 forms insertion opening 311. Inside shield frame 315, in addition to contacts (spring probes 312) to be connected to sensors (electrodes 133) of sensor sheet 100, an external contact (USB port 313) for connection to an external device is provided. Upon attachment of packing 141, the inside of shield frame 315 in which the contacts are provided is shielded from the outside.

Consequently, as illustrated in FIG. 4B, upon insertion of packing 141 to insertion opening 311 in the back surface of terminal 300, spring probes 312 are brought into abutment with the terminal ends of wires 132, the terminal ends being exposed on tongue piece 131, at a predetermined pressure, whereby the spring probes 312 and the wires 132 are electrically interconnected, respectively. Also, in this state, the inner side surrounded by packing 141 is prevented from entry of water from the outside. In other words, the plurality of spring probes 312 and the plurality of wires 132 are electrically connected without short-circuiting caused by water.

Furthermore, inside insertion opening 311, USB port 313 is disposed in addition to spring probes 312, and thus, when electrocardiographic measurement is being performed with terminal 300 attached to sensor sheet 100, USB port 313 cannot be used. Consequently, the risk of electrical shock caused by connection of an external electronic device to USB port 313 during electrocardiograph measurement can reliably be eliminated. In other words, in the present embodiment, the contacts for electrocardiographic measurement (spring probes 312) and USB port 313 are prevented from being connected simultaneously to ensure safety. Furthermore, the contacts for electrocardiographic measurement (spring probes 312) and USB port 313 are housed inside packing 141 and are thus waterproofed at the same time. In other words, both waterproofing and safety can be ensured by the simple configuration.

Furthermore, as illustrated in FIGS. 5A and 5B, wide portion 150 is formed at a distal end of tongue piece 131. Also, locking cut 314 is formed in the back surface of terminal 300. Upon insertion of packing 141 of connector 140 to insertion opening 311, wide portion 150 of tongue piece 131 engages with locking cut 314, whereby terminal 300 is locked by tongue piece 131 so as not to move in the arrow Z direction (direction around the ground where terminal 300 is attached).

Furthermore, hook-and-loop fastener 160 is firmly fixed to the front surface side of upper sheet 120. Hook-and-loop fastener 160 can be stuck to hook-and-loop fastener 320 provided on the back side of terminal 300.

Consequently, upon insertion of packing 141 to insertion opening 311, terminal 300 is held on sensor sheet 100 by engagement between tongue piece 131 and locking cut 314 and joining between hook-and-loop fasteners 160, 320. Here, hook-and-loop fasteners 160, 320 have only a small holding force in a direction perpendicular to the surface, but have a large force in the surface direction. Therefore, tongue piece 131 and hook-and-loop fasteners 160, 320 reliably prevent terminal 300 from dropping in the surface direction.

Here, terminal 300 engages with tongue piece 131 at an upper portion and thereby hang down with tongue piece 131 as an axis. Upon terminal 300 being lightly pushed to the sensor sheet 100 side (that is, the subject side) in this state, hook-and-loop fasteners 160, 320 are joined to each other and terminal 300 are thereby prevented from wobbling. In fact, terminal 300 is held by tongue piece 131 so as to be at least partly floated from sensor sheet 100.

The subject perceives terminal 300 via the skin at the part of the joining between tongue piece 131 and the packing 141 and the part of the joining between hook-and-loop fasteners 160, 320, and as a result, for example, a feeling of discomfort the subject have due to the presence of terminal 300 can be reduced compared to a case where the entire back surface of terminal 300 is firmly fixed to sensor sheet 100. A further decrease in area of hook-and-loop fasteners 160, 320 enables further reduction of a feeling of discomfort the subject has.

Furthermore, hook-and-loop fastener 160 is disposed at a position corresponding to gel 134. Consequently, the gel serves as a buffer, which makes the subject be less likely to feel the presence of terminal 300.

Instead of hook-and-loop fasteners 160, 320, for example, a snap fastener or magnets may be used. In brief, any various rejoinable joining devices can be used. Also, terminal 300 may be held by tongue piece 131 alone or tongue piece 131 and the connector, without using hook-and-loop fasteners 160, 320, a snap button, magnets or the like.

Advantageous Effect of Embodiment

As described above, according to the present embodiment, as a result of terminal 300 being attached to sensor sheet 100 using tongue piece 131 extending from sensor sheet 100, for example, a feeling of discomfort a subject has due to the presence of terminal 300 can be reduced compared to a case where the entire back surface of the terminal 300 is firmly fixed to sensor sheet 100, enabling provision of a biological information measurement apparatus that can reduce a feeling of discomfort a subject has when the subject wears the biological information measurement apparatus.

Also, since the tongue piece 131 is provided with connector 140 to which a connector (shield frame 315 and insertion opening 311) of terminal 300 is to be connected, engagement via tongue piece 131 and engagement via connector 140 enable terminal 300 to be firmly held on sensor sheet 100. Also, tongue piece 131 enables both mechanical and electrical joining of terminal 300 to sensor sheet 100 at a time, enabling saving user's trouble. However, electrical connection of terminal 300 to sensor sheet 100 may be provided in a part other than tongue piece 131.

Furthermore, provision of rejoinable joining devices such as hook-and-loop fasteners 320, 160 are provided in terminal 300 and sensor sheet 100, respectively, enables terminal 300 to be further firmly held on sensor sheet 100.

Furthermore, provision of gel 134 between hook-and-loop fasteners 320, 160 and the skin can reduce a feeling of discomfort given where hook-and-loop fasteners 320, 160 are used. Here, a buffer other than the gel 134, such as a sponge, may be disposed between the rejoinable joining devices such as hook-and-loop fasteners 320, 160 and the skin of the subject. However, in the present embodiment, gel 134, which is used for enhancement in electric conductivity, is used also as a buffer, providing the advantage of avoiding an increase in number of components.

Although the above embodiment has been described in terms of a sensor sheet according to the present invention in which all of electrodes 133 are held inside single sheets 110, 120, the present invention is applicable to a sheet in which in electrodes 133 are disposed on individual sheets and electrodes 133 are interconnected via lead wires to be not applied to a subject. However, in the above embodiment, electrodes 133, wires 132 and tongue piece 131 are integrally formed, and thus, a signal with small noise can be obtained in comparison to a configuration in which electrodes 133, wires 132 and tongue piece 131 are formed separately and interconnected via cables or connection sections.

Also, although the above embodiment has been described in terms of the case where electric circuit section 130 including, e.g., wires 132 and electrodes 133 is mounted in sensor sheet 100, a sensor mounted in a sensor sheet according to the present invention is not limited to electric circuit section 130. For example, an optical component for measuring $SpO_2$ may be mounted as the sensor. The sensor to be mounted in the sensor sheet may be selected according to the object to be measured.

Also, although the above embodiment has been described in terms of the case where electric circuit section 130, which serves as the sensor, is disposed between lower sheet 110 and upper sheet 120, the sensor may be disposed on upper sheet 120.

Also, although the above embodiment has been described in terms of the case where the center area of sensor sheet 100 has a multi-layer structure including lower sheet 110 and upper sheet 120, the center area may have a single-layer structure including upper sheet 120 alone with no lower sheet 110 provided. Even in such case, upper sheet 120 is made to be higher in strength than lower sheet 110, enabling provision of both a force for holding the sensor in the center area and the capability of following the skin in peripheral edge portion 110a.

Also, although the above embodiment has been described in terms of the case where tongue piece 131 is formed separately from upper sheet 120, tongue piece 131 may be formed integrally with upper sheet 120. In other words, tongue piece 131 may be provided so as to extend from upper sheet 120.

Furthermore, a tongue piece may extend from the terminal 300 side. In other words, a terminal only needs to be attached to a sensor sheet so as to be at least partially floated from the sensor sheet by a tongue piece. Consequently, the terminal is prevented from coming into direct contact with the skin or the sensor sheet, enabling reducing a feeling of discomfort the subject has due to the presence of the terminal and thus enabling reducing a feeling of discomfort the subject has when the subject wears the biological information measurement apparatus.

Furthermore, although the above embodiment has been described in terms of a case where a sensor sheet according to the present invention is applied to the chest region of a subject in use, a sensor sheet according to the present invention may be applied not only to the chest region, but also regions other than the chest region, such as the abdominal region or the back, of a subject in use. In brief, a sensor sheet according to the present invention can arbitrarily be applied to a region suitable for obtainment of biological information.

The above embodiments are mere specific examples for carrying out the present invention and the technical scope of the present invention should not be limited by these embodiments. In other words, the present invention can be carried out in various modes without departing from the spirit or the main features of the invention.

The present application claims priority based on Japanese Patent Application No. 2015-179595 filed on Sep. 11, 2015. The entire disclosures in the descriptions and the drawings in these applications are incorporated herein by reference.

INDUSTRIAL APPLICABILITY

The present invention is applicable to a biological information measurement apparatus that measures including biological information using a sensor sheet applied to the skin of a subject and a terminal attached to the sensor sheet.

REFERENCE SIGNS LIST 100 sensor sheet
110 lower sheet
110a peripheral edge portion
120 upper sheet
130 electric circuit section
131 tongue piece
132 wire
133 electrode
134 gel
140 connector
141 packing
150 wide portion
160, 320 hook-and-loop fastener
210 liner
220 top separator
300 terminal
310 attachment section
311 insertion opening
312 spring probe
313 USB port
314 locking cut
315 shield frame

The invention claimed is:

1. A biological information measurement apparatus, comprising:
a sensor sheet including a surface side and a skin side, the skin side of the sensor sheet to be applied to a skin of a subject;
a terminal to be attached to the sensor sheet, the terminal including an insertion opening and a locking cut in a back surface of the terminal;
a tongue piece including a connector that protrudes from the surface side of the sensor sheet and having a wider portion formed at a distal end of the tongue piece, wherein upon insertion of the connector to the insertion opening of the terminal, the connector engages with the insertion opening and the wider portion engages with the locking cut of the terminal to removably attach the terminal to the sensor sheet via the tongue piece,
wherein when the tongue piece is removably attached to the terminal, the terminal is at least partially spaced apart from the sensor sheet; and
a rejoinable joining device including at least two pieces, a first piece of the rejoinable joining device being fixed to the surface side of the sensor sheet and a second piece of the rejoinable joining device being fixed to a back surface of the terminal,
wherein the rejoinable joining device is located near the distal end of the tongue piece, and the terminal is further attached removably to the sensor sheet via the first and second pieces of the rejoinable joining device, wherein
the sensor sheet includes a first sheet to be applied to the skin of the subject, a second sheet stuck to a front surface side of the first sheet, and an electric circuit section including the tongue piece, a wire extending from the tongue piece, and an electrode formed at a terminal end of the wire which are integrally formed on a base material, the base material being interposed between the first sheet and the second sheet, and
the second sheet has a thickness larger than that of the first sheet.

2. The biological information measurement apparatus according to claim 1, wherein:
the tongue piece extends from a center area of the sensor sheet; and
the terminal is attached to the center area of the sensor sheet so as to be at least partially floated from the sensor sheet.

3. The biological information measurement apparatus according to claim 1, wherein a buffer is disposed between the rejoinable joining device and the skin of the subject.

4. The biological information measurement apparatus according to claim 3, wherein the buffer comprises a gel.

5. The biological information measurement apparatus according to claim 1, wherein the tongue piece extends from the base material.

6. A biological information measurement apparatus, comprising:
a sensor sheet including a surface side and a skin side, the skin side of the sensor sheet to be applied to a skin of a subject;
a terminal to be attached to the sensor sheet, the terminal including an insertion opening and a locking cut in a back surface of the terminal; and
a tongue piece including a connector that protrudes from the surface side of the sensor sheet and having a wider portion formed at a distal end of the tongue piece, wherein upon insertion of the connector to the insertion opening of the terminal, the connector engages with the insertion opening and the wider portion engages with the locking cut of the terminal to removably attach the terminal to the sensor sheet via the tongue piece, wherein when the tongue piece is removably attached to the terminal, the terminal is at least partially spaced apart from the sensor sheet, wherein:

the sensor sheet includes a first sheet, a bottom side of the first sheet to be applied to the skin of the subject, a second sheet stuck to a top side of the first sheet, and an electric circuit section including the tongue piece, a wire extending from the tongue piece, and an electrode formed at a terminal end of the wire which are integrally formed on a base material, the base material being interposed between the first sheet and the second sheet;

the tongue piece is connected to the wire and protrudes through a top side of the second sheet through a hole in the second sheet from the interposed position between the first and second sheets; and the second sheet has a thickness larger than that of the first sheet.

7. The biological information measurement apparatus according to claim 1, wherein the tongue piece is thicker than the base material of the wire.

8. The biological information measurement apparatus according to claim 6, wherein the tongue piece is thicker than the base material of the wire.

9. The biological information measurement apparatus according to claim 1, wherein:
the second sheet is smaller in area than the first sheet; and
the area of the second sheet is large enough to cover the electric circuit section.

10. The biological information measurement apparatus according to claim 1, wherein at least the first sheet of the first and second sheets is formed of polyurethane.

11. The biological information measurement apparatus according to claim 1, wherein the first sheet has a thickness of no more than 20 μm.

12. The biological information measurement apparatus according to claim 1, wherein:
the base material is formed of polyethylene terephthalate (PET) or polyethylene naphthalate (PEN); and
the wire is formed in a meandering pattern, a shallow curve, or a linear fashion.

* * * * *